United States Patent [19]

Pagliai

[11] Patent Number: 4,651,903

[45] Date of Patent: Mar. 24, 1987

[54] MOTORIZED PUMP PRESSURIZED LIQUID SPRAYER

[76] Inventor: Ferro D. Pagliai, 1300 Mairette Rd., Pacific Palisades, Calif. 90272

[21] Appl. No.: 854,093

[22] Filed: Apr. 21, 1986

[51] Int. Cl.$^4$ .............................................. B67D 5/64
[52] U.S. Cl. .................................... 222/175; 222/333; 239/153; 239/332; 417/234
[58] Field of Search ............... 239/152, 153, 154, 332; 417/234; 248/674; 222/175, 333, 606, 626

[56] References Cited

U.S. PATENT DOCUMENTS

| | | |
|---|---|---|
| 1,641,735 | 9/1927 | Cheeseman . |
| 2,162,057 | 6/1939 | Brandt . |
| 2,192,256 | 3/1940 | Brandt . |
| 2,429,773 | 10/1947 | Root . |
| 2,881,555 | 4/1959 | Atkinson, Sr. . |
| 2,958,155 | 11/1960 | Emmerich ............................. 222/175 |
| 3,015,281 | 1/1962 | Umholtz ............................... 417/234 |
| 3,199,785 | 8/1965 | Schmierer ............................ 239/153 |
| 3,320,895 | 5/1967 | Peterson et al. ..................... 222/626 |
| 3,386,622 | 6/1968 | Cox . |
| 3,421,697 | 1/1969 | Marks .................................. 239/152 |
| 3,901,449 | 8/1975 | Bochmann ........................... 239/332 |
| 3,966,092 | 6/1976 | Ballu .................................... 222/175 |
| 4,600,129 | 7/1986 | Kordo ................................... 222/175 |

Primary Examiner—H. Grant Skaggs
Attorney, Agent, or Firm—Gausewitz, Carr & Rothenberg

[57] ABSTRACT

Sprayer apparatus with a molded container having a back-support panel for abutting relation with the back of a user while being carried, the container having attached, at the lower end thereof, a stand formed of bent tubing for supporting the container in a vertical position on a surface. A pressure vessel is centrally disposed within the container, with the lower portion of the pressure vessel having a threaded coupling fitting opening communicating with inlet and outlet passages. A fitting is threadably received within this opening, the fitting having passages communicating with the container and pressure vessel. A support plate is configured for detachably slidably securing directly to the lower part of the stand for support of a motor operated pump and battery, with the battery disposed inwardly relative to the bend of the stand, and the motor-pump outwardly thereof. Flexible tubing interconnects the pump and fitting. The motor-pump assembly is thus attached at the lowest part of the apparatus for stability, with the center of gravity of the motor-pump assembly generally centrally located relative to the lateral dimensin of the apparatus, and generally in line with the longitudinal centerline of the container. The assembly of support plate, battery, pump, motor and fitting is arranged as a unitary retrofit package to update the manual pump assembly of an existing sprayer, thus converting the manual sprayer into a motorized sprayer.

22 Claims, 4 Drawing Figures

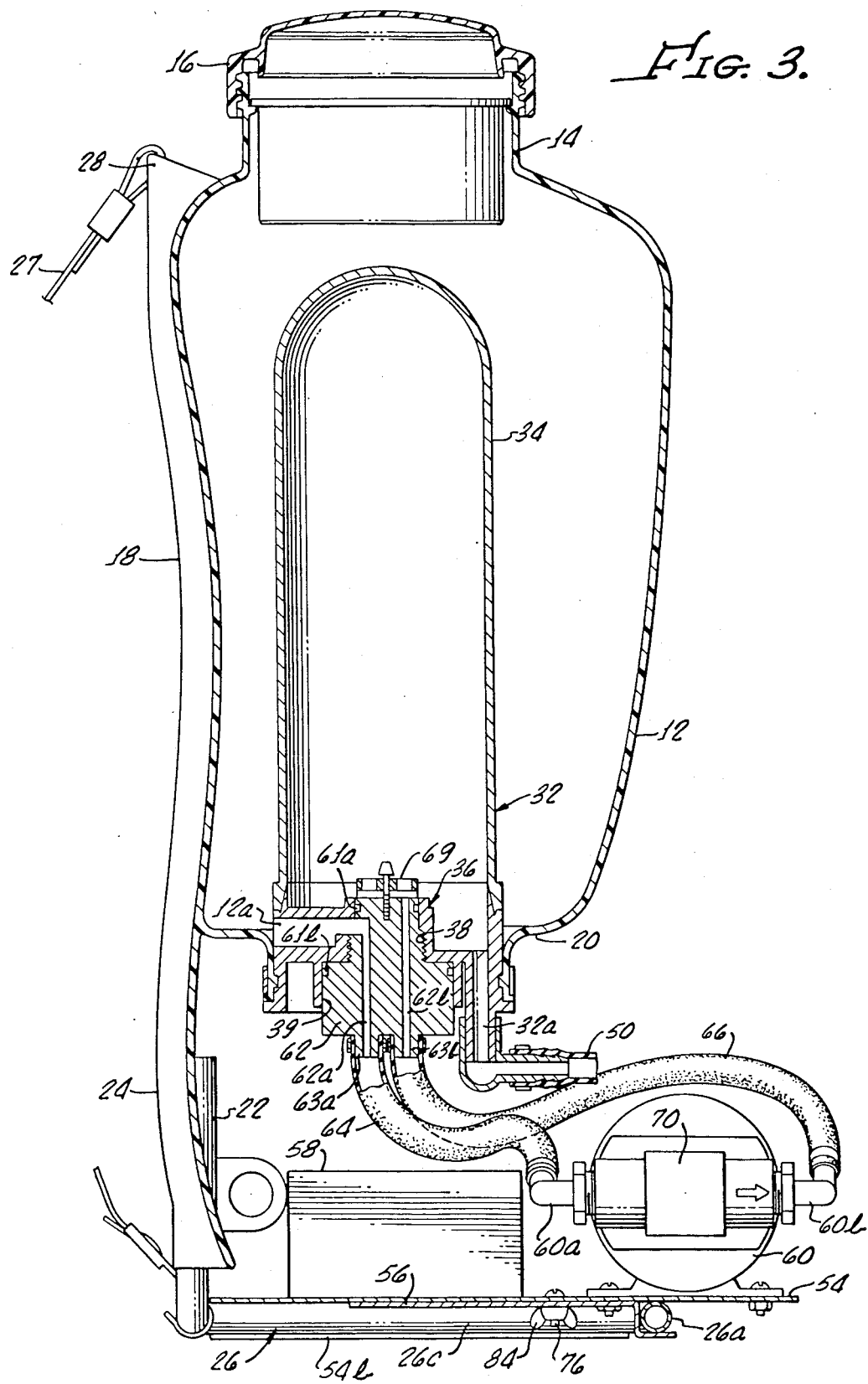

MOTORIZED PUMP PRESSURIZED LIQUID SPRAYER

BACKGROUND OF THE INVENTION

The background of the invention will be discussed in two parts.

1. Field of the Invention

The present invention relates to portable, high liquid volume, back-carried sprayers of pressurized liquids, and more particularly to such a sprayer which includes a battery pack and motorized pump arrangement.

2. Description of the Prior Art

Sprayers intended for the dispensing of liquid disinfectants, insecticides, fertilizers, pest exterminating liquids and other residential or agricultural-type treatment liquids normally contain a reservoir or tank for carrying of the liquids therein. Such sprayers are normally designed for portability, such as carrying by hand, or on the back, by use of webbing or straps connected to the sprayer in such a manner that the straps enable the sprayer to be carried by the shoulders and back of the user. Such sprayers normally include a manually operated lever actuated pump which is actuable by the user for dispensing the liquids through a hose. In some such sprayers, to avoid a need for continually operating the lever while dispensing liquids, an internal pressure tank is employed, whereby the internal tank may be placed under pressure by actuation of the lever with, or without, dispensing of fluids. In such sprayers, liquid discharge flows more continuously as a conseqeunce of the pressure. One such pressurized garden sprayer is shown and described in U.S. Pat. No. 2,162,057, entitled "Knapsack Sprayer", issued to H. Brandt et al on June 13, 1939. Other manually operated portable garden sprayers are shown in U.S. Pat. Nos. 2,192,256, entitled "Sprayer With Agitator", issued to Brandt on Mar. 5, 1940; and 3,966,092, entitled "Manually Operated Man-Portable Sprayer", issued to Ballu on June 29, 1976.

Some liquid sprayers, and even some dusters for discharging liquids or particulate matter have been developed with electrically operated pump or blower arrangements. The following patents exemplify the prior art relating to such aparatus: U.S. Pat. Nos. 2,429,773, entitled "Dusting Apparatus", issued Oct. 28, 1947 to Root; 2,881,555, entitled "Crop Duster", issued Apr. 14, 1959 to Atkinson, Sr., et al; 3,386,622, entitled "Portable, Self-Contained Electrical Pumping Device", issued June 4, 1968 to Cox et al; 3,421,697, entitled "Spraying Equipment", issued Jan. 14, 1969 to Marks; and 3,901,449, entitled "Cordless Electric Sprayer", issued Aug. 26, 1975 to Bochmann. Such prior art sprayers and dusters provide motors for driving pumps and blowers with little regard to the placement of the heavier parts of the apparatus, thus rendering the carrying of such apparatus uncomfortable and potentially hazardous. Furthermore, although in most instance, such apparatus include some form of base for support, when partially full and placed on the ground, the center of gravity of the apparatus is unduly high, thus providing instability at rest.

Exemplary of such prior art motor operated apparatus is U.S. Pat. No. 3,199,785, entitled "Portable Spraying Device and Support", issued Aug. 10, 1965 to Schmierer. The sprayer is gasoline motor operated and includes an integrally formed back support and receptacle with the support having integrally formed provision for attachment of the gasoline engine thereto. Attached to the support, below the engine arrangement, is a frame formed of metallic tubing, bent at an angle to serve as a stand to support the apparatus on a surface. As part of the apparatus an attempt is made to provide stability by placing the center of gravity of the engine inwardly of the limits of the stand. However, with such an arrangement with the receptacle at the very top and the engine mounted generally centrally relative to the vertical standing position, the overall center of gravity is high, thus creating a tendency to readily tip if impacted from the front or rear. The container and support of the '785 patent are specifically formed for the engine utilized, and they cannot be used with any other existing apparatus.

High volume agricultural sprayers in use today are mainly manual or gasoline engine powered. With gasoline engines as a source of power, prior art apparatus have limitations on location and timing of use. Such gasoline engines are limited in usage to outdoor locations, and in most instances, because of noise pollution, are limited in use to certain times of the day. Such sprayers cannot be used, for example, indoors, such as in a hospital, or the like, to spray disinfectants.

It is accordingly an object of the present invention to provide an agricultural, insecticide, or disinfectant sprayer that avoids or minimizes the above-mentioned disadvantages.

SUMMARY OF THE INVENTION

In carrying out principles of the present invention, in accordance with a preferred embodiment thereof, the sprayer is provided with a molded container having a surface thereof configured for abutting relation with the back of a user while being carried, the container having provision at the lower end thereof for attachment of a stand formed of bent tubing disposed to support the container in a vertical position on a surface. A pressure vessel is centrally disposed within the container, with the lower portion of the pressure vessel having a threaded opening communicating with inlet and outlet passages. A fitting is threadably received within this opening, the fitting having passages communicating with the container passages with nipples on the fitting adapted for attachment to tubing. A support plate is configured for detachably securing directly to the lower part of the stand for support of a motor operated pump and battery, with the battery disposed inwardly relative to the bend of the stand, and the motor-pump outwardly thereof. Flexible tubing interconnects the pump and fitting. The motor-pump assembly is thus attached at the lowest part of the apparatus for stability, with the center of gravity of the motor-pump assembly generally centrally located relative to the lateral dimension of the apparatus, and generally in line with the longitudinal centerline of the container. Also described is a retrofit package of a support, battery, pump, motor and fitting specifically arranged to replace the manual pump of prior sprayers now presently used.

Other objects, features and advantages of the invention will become apparent from a reading of the specification, when taken in conjunction with the drawings, in which like reference numerals refer to like elements in the several views.

BRIEF DESCRIPTION OF THE DRAWINGS

FIG. 3 is a side elevational view, partially in crossection, and partially broken away, of the agricultural sprayer of FIG. 2.

DETAILED DESCRIPTION OF THE PREFERRED EMBODIMENT

Figure 1:
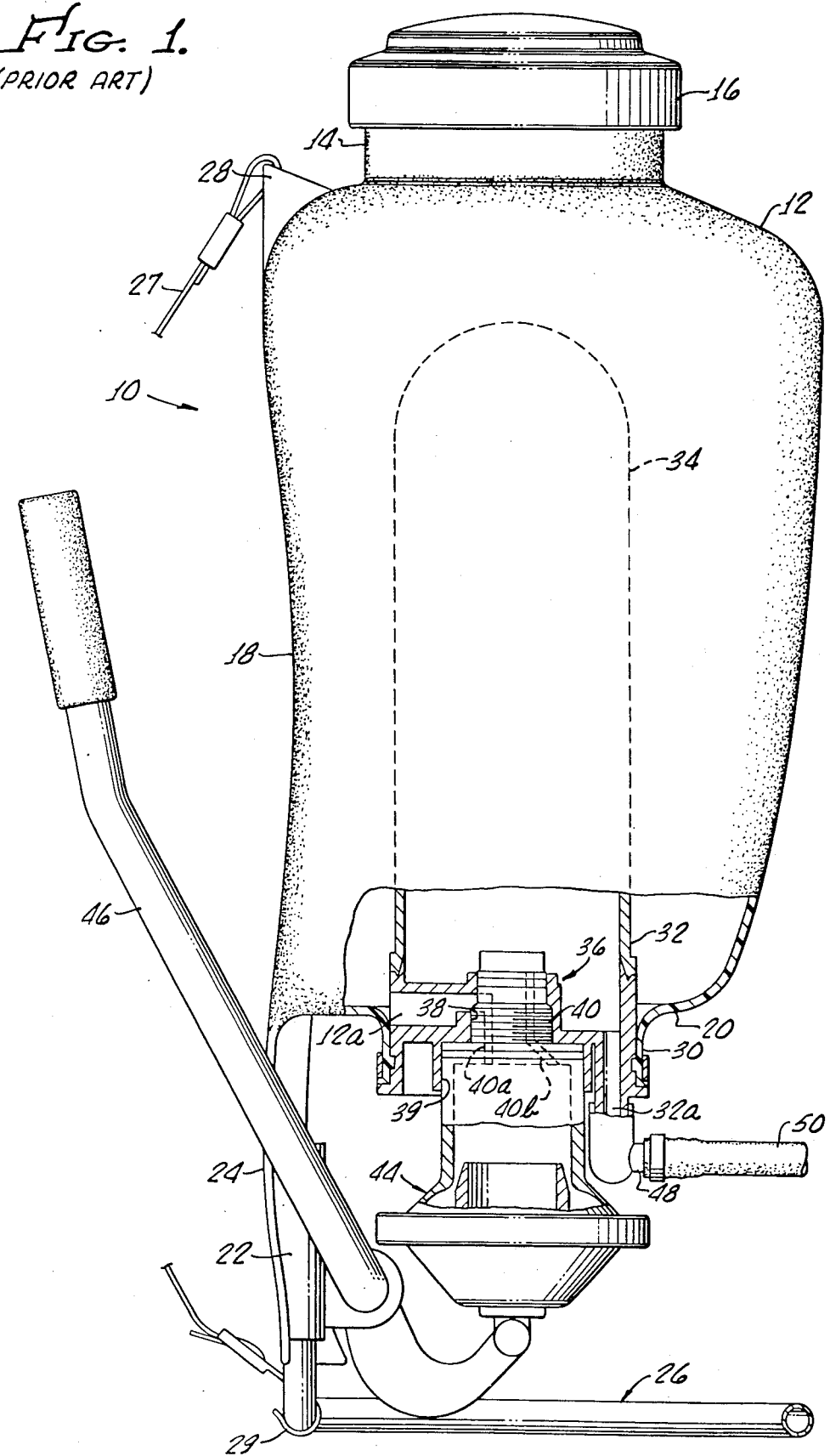
FIG. 1 is a side elevational view, partially in cross-section and partially broken away, of a prior art agricultural sprayer arrangement.

FIG. 1 depicts a high volume sprayer for dispensing agricultural liquids, disinfectants, insecticides, herbicides and the like, generally designated 10, of a type that is now widely used, the sprayer 10 including a reservoir or container 12 formed of a plastic body having a fill neck 14 providing an opening that is closed and sealed by a detachable cap 16. The container 12 is configured for containing a substantial amount of liquid, such as several gallons. A back-supporting panel 18 is fixed to or integrally formed with a forward wall of the container 12 and extends downwardly for a sufficient distance below the bottom 20 of the container. A pair of integral lugs 22 (only one of which is shown), on a lower section 24 of the back panel 18 that extends below the container 12 are provided with vertical bores that fixedly receive and support legs of a tubular stand or container support frame, generally designated 26. The stand 26 is formed in such a manner that it can support the sprayer 10 in a generally vertical position on a surface, whether the container 12 is full, partially full or empty. Back panel 18 is contoured to snugly fit against the back of a person to whom the container may be secured by means of straps 27 suitably attached to upper and lower portions 28, 29, respectively, of the back panel 18.

The bottom of the container 12 is formed with a downwardly extending neck 30, defining an opening in which is mounted the lower portion of a generally cylindrical pressure vessel 32, having an upper section 34 (shown in dotted lines) extending upwardly into the interior of the container 12. A pressure relief valve (not shown) may be mounted in the top of pressure vessel 12. The lower section of the pressure vessel 32 is formed with a pump receiving fitting, generally indicated at 36, that includes an inner neck section having an internally threaded opening 38 and an enlarged outer neck section having an enlarged diameter opening 39. The internally threaded opening 38 is configured to detachably receive an externally threaded valve section and connecting fitting 40 of a manually operated pump assembly, generally designated 44, actuated by a lever 46 pivotally coupled to a pair of bearing lugs 47 (only one of which is shown) integrally formed rearwardly of the lower section 24 of the back support 18.

In such sprayers 10, actuation of the lever 46 operates the pump 44 in alternate suction and discharge strokes, respectively, to draw in liquid from the container 12 through an inlet passage 12a communicating with a fitting passage 40a (shown in dotted lines), and to expel liquid from the pump 44 chamber under pressure into the pressure vessel 32 through fitting passage 40b (shown in dotted lines). Liquid from the pressure vessel 32 is then selectively discharged through outlet passage 32a to the exterior via tubing fitting 48 which is connected to a hose 50, the other end of which is connected to a manually controllable sprayer nozzle (not shown). Although not shown, it is to be understood that any or all of the passages may have suitable check valve means for enabling fluid passage in one direction only.

Figure 2:
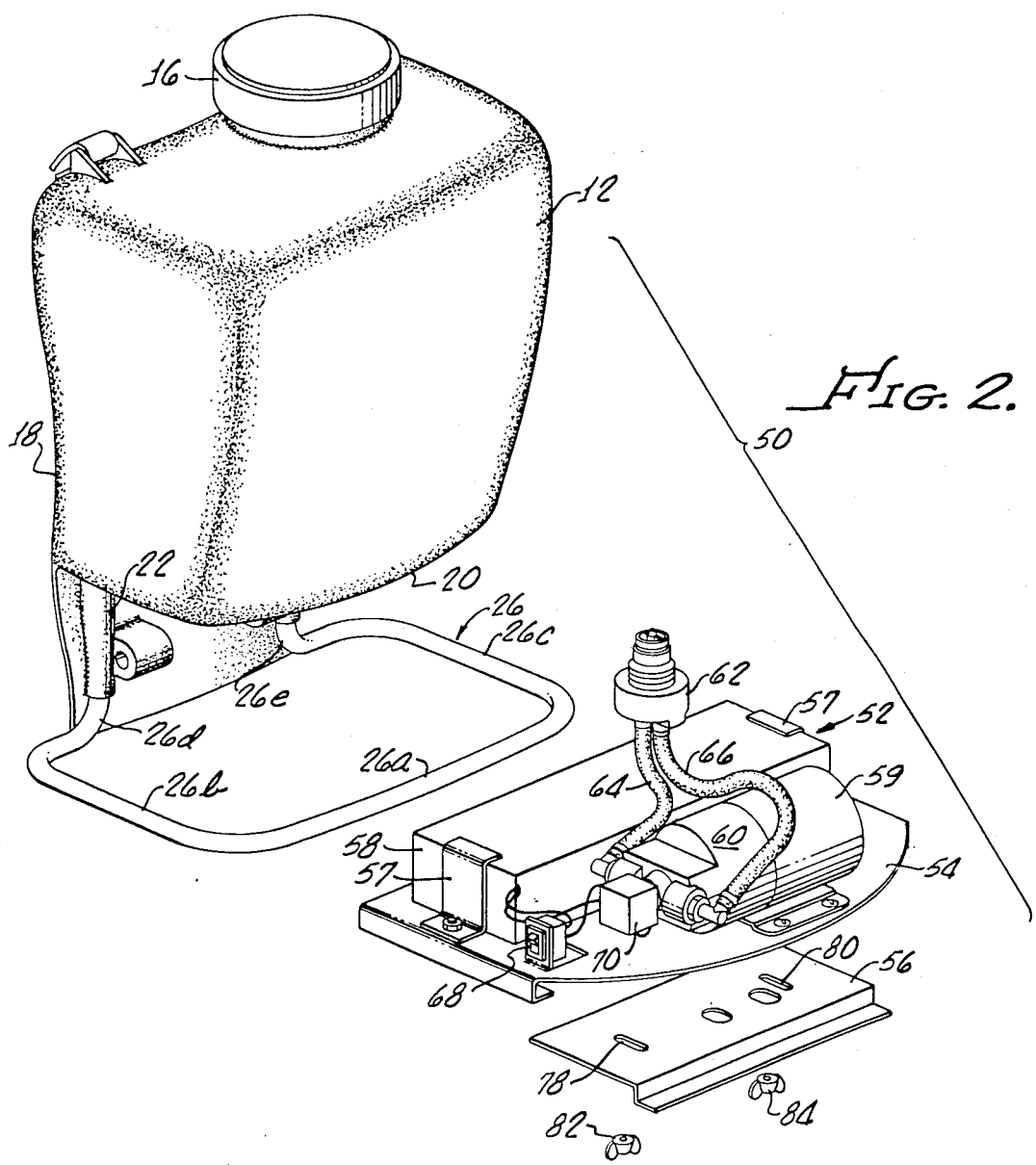
FIG. 2 is an exploded perspective view of an agricultural sprayer embodying principles of the present invention, showing the unitary retrofit package of support plate, battery, motor, pump and fitting.
Figure 4:
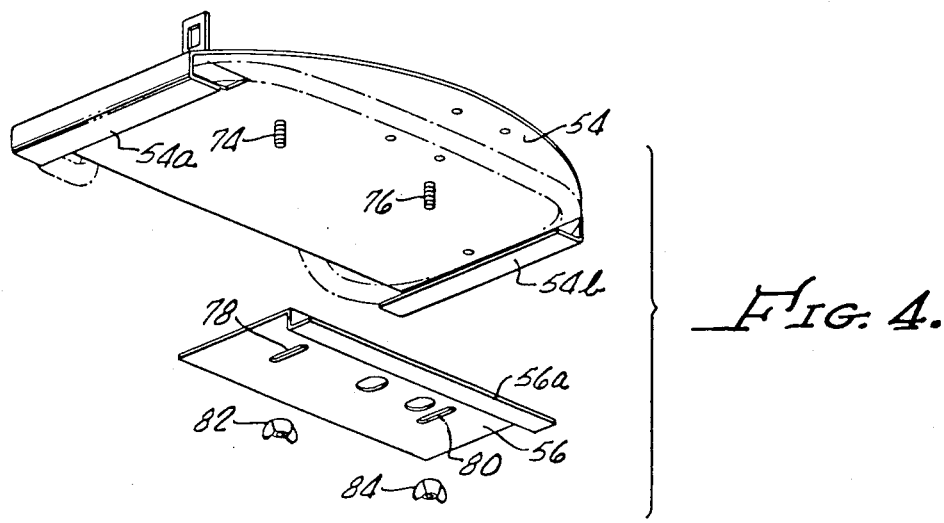
FIG. 4 is an exploded bottom perspective view of the support plate assembly used in the agricultural sprayer of FIG. 2.

Referring now to FIGS. 2 through 4, there is shown a sprayer apparatus, generally designated 50, in accordance with the present invention. Sprayer 50 is functionally similar to the sprayer of FIG. 1, having the identical, or similar, container, pressure vessel, and tubular support stand, but has an electric powered pump package substituted for the manual pump. Basically, the sprayer 10 of FIG. 1 has had certain parts removed, primarily the pump 44 and the actuating lever 46, thus leaving the parts shown in FIG. 2, that is, the container 12 with its integral back support 18 with the tubular stand 26 attached thereto. As shown in FIG. 2, the stand 26 of the prior sprayer is formed from a length of tubular material, such as aluminum, with a main generally rectangularly configured portion including front portion 26a, and side portions 26b and 26c shaped to form a rectangular base for support of the container 12. For this purpose, the opposite ends 26d and 26e of the tubing are bent at right angles upwardly to the plane of the base portion for attachment within lugs 22. The dimensions of the base portion of the stand 26, that is the distance between side tubing portions 26b and 26c and the length thereof, generally correspond to the outer dimensions of the container 12 when viewed from the top.

In accordance with the present invention, a motor operated pump assembly, generally designated 52, is configured as a complete unitary retrofit package for readily adapting such a prior art sprayer 10 into a motorized sprayer 50, with minimum of effort, while providing ease of carrying, with a stable and low center of gravity. In addition, with a battery operated system, the sprayer 50 is quiet, does not emit noxious fumes, and may be used at any time of day, and may be used indoors for spraying disinfectants and the like. For this purpose, a support plate assembly, including upper plate 54 and lower plate 56 are configured for attachment to the base portion of the stand 26. Assembled to the upper support plate 54 are a battery 58 and an assembly including a motor 59 and a pump 60. For interconnection with the container 12, a fitting 62 is provided with provision for connection of flexible tubing 64 and 66 thereto, and to the pump 60. An electrical switch 68 is also attached to the upper support plate 54 for connection between the motor 59 and the battery 58. Support plate 54 may have other configurations and may be made of suitable materials, whether metal or plastic. The plates 54 and 56 may be perforated, or formed as a skeleton frame, and may have other tube attachment means that allow ready assembly and disassembly of the retrofit package to the container stand 26.

As better illustrated in FIG. 3, the fitting 62 is formed externally as a replacement for the fitting 40 of the manual pump. It is configured with an upper threaded portion which is threadably inserted into the threaded opening 38 of the neck 36 within the pressure vessel 32. The lower enlarged diameter portion mates with the enlarged diameter opening 39, with both portions suitably sealed such as by means of O-rings 61a and 61b about the periphery of the upper and lower portions of fitting 62 between the body thereof and the openings 38 and 39, respectively. Thus, it cooperates with, and seals to the pressure vessel 32 and container 12 precisely as does the manual pump fitting 40, which it replaces. The fitting 62 is provided with a first passage 62a for fluid flow communication with passage 12a of container 12, and a second passage 62b for fluid flow communication with the interior of pressure vessel 32. At the lower end of fitting 62, there are provided two integrally formed tubular extensions 63a and 63b to which are attached flexible hoses 64 and 66, respectively.

Passage 62a and hose 64 form an exit passage for liquid from the interior of container 12 to the suction inlet 60a of the pump 60. The outlet 60b of the pump 60 returns the liquid passing therethrough, under pressure, through hose 66 to the passage 62b of fitting 62 to the interior of pressure vessel 32. A valve member 69 on the upper edge of the fitting 62 acts as a check valve for liquid entering the pressure vessel 32. As pressure is applied from passage 62b, the valve member 69 moves away from the opening of passage 62b, permitting fluid entry. When the pump 60 is inoperative, the valve member 69 closes the passage 62b.

To limit the amount of pressure within the pressure vessel 32, and to enable automatic actuation of the motor 59 when needed, a pressure switch 70, is attached to the plate 54 and electrically placed in series with the switch 68, the battery 58 and the motor 59. Although not shown in detail, as is conventional with such pressure switches 70, a threaded fitting thereof contains an opening for sensing line pressure, which operates a diaphragm or bellows, with switch contact made or broken in response to movement of the diaphragm or bellows. The series connection of the electrical components is likewise straightforward, and an explanation thereof is deemed unnecessary to an understanding of the invention.

As shown in the drawings, the support plates 54 and 56 are configured for detachable connection to the base portion 26a of stand 26. For this purpose, upper support plate 54 is a generally planar member which has the opposing lateral edges thereof bent downwardly and inwardly to form C-shaped channel portions 54a and 54b, each open at front and back, or at least at the front, for slidably engaging the side tubing portions 26b and 26c of the base portion of the stand 26. The lower support plate 56 has a lateral dimension less than the distance between the side tubing portions 26b and 26c, and has the front edge thereof bent to form a clamping bracket 56a for engagement with the lower side of the front interconnecting tubing portion 26a of the stand 26. For clampimg, the upper plate member is provided with first and second bolt members 74 and 76 extending downwardly therethrough in alignment with first and second slotted openings 78 and 80, respectively, formed in the lower plate member, with the bolt members engaging wing nuts 82 and 84, respectively.

As shown in FIG. 3, the support plates 54 and 56 are in planar abutting rellation, when secured to the base portion of the stand 26, with the clamping portion 56a of the lower plate 56 clampingly engaging the front tubing portion 26a. The rear edge of the upper plate 54 is configured for generally abutting the orthogonally disposed tubing ends 26d and 26e of the stand 26, with the channel portions 54a and 54b encircling the side tubing portions 26b and 26c, respectively, of the stand 26.

Secured to the upper surface of the upper plate 54 is the battery 58, which has an elongate box-like form, centrally positioned relative to the long dimension of the plate 54, and rearwardly positioned relative to the front tubing portion 26a of the stand 26. The battery 58 is secured to the plate 54 closely adjacent the lower section 24 of the back panel by means of generally Z-shaped clamping brackets 57, the upper ends of which engage the upper surface of the battery 58, and the lower ends of which are attached to the plate 54 by sheet metal screw means or the like. The motor 59 and pump 60, as an assembly, are mounted forwardly of the side of the battery 58, but in proximate relation thereto, with the center of gravity of both the battery 58 and the motor/pump assembly being generally along a line bisecting the distance between the side tubing portions 26b and 26c of stand 26. In this manner, the center of gravity of the motor operated pump assembly 52 lies generally at the midpoint of the rectangularly configured base portion of the stand 26.

With this arrangement, the stand 26 serves a dual function, that is, as a base for support of the sprayer 50 and as a means for receiving, in readily detachable manner, the motor-operated pump assembly 52. With the relatively heavy mass of the motor operated pump asssembly attached at the lowest point of the sprayer 50, the overall center of gravity of the sprayer 50 is lower than with the conventional sprayer 10 of FIG. 1, thus providing greater stability for the sprayer 50 when supported on a surface. Moreover, the relative configuration and positioning of the battery 58 and motor-pump assembly, one behind the other, and the nature of the battery attaching brackets 57, permit ready removal and replacement of the battery 58. This may be done without removing the motor-pump assembly by removing one of the brackets 57 and sliding the battery 58 out to the side of the support plate 54. The battery 58 is encased in a sealing cover to protect it from the effects of liquid that may spill during filling of the containers. Furthermore, with the lower center of gravity, when sprayer 50 is worn on the back, and with the heavy battery 58 located adjacent the user, the additional weight occasioned by the assembly 50 lies closer to the hips of the user, thus providing more comfort for extended periods of use.

In accordance with the present invention, there has been shown and described an electrical motor-operated pump driven portable sprayer 50, of stable configuration with the parts thereof positioned for ease of assembly and disassembly, and ease of wear. Additionally, the motor-operated pump assembly 52 and fitting 62 may be readily assembled to an existing manually operated pump sprayer 10 having a coupling fitting on the container thereof, with appropriate configuration of the fitting 62 to the liquid flow passages of the container fitting. An existing manual sprayer can be readily converted to a motorized sprayer by unscrewing the fitting and removing the manual pump assembly and pump operating handle, and sliding the motor pump assembly support plate on to the container support frame 26, connecting clamping plate 56 to support plate 54, and threading fitting 62 into the pump receiving coupling fitting 36 of the pressure vessel 32.

With the battery operation, the sprayer 50 is quiet, and may be used at any time of day without creating noise pollution. Furthermore, since it does not emit noxious fumes which would be emitted by an internal combustion engine, it may readily be used indoors, such as in residences, hospitals, and the like for spraying pest exterminating liquids or disinfectants. While there has been shown and described a preferred embodiment, it is to be understood that various other adaptations and modifications may be made within the spirit and scope of the invention.

I claim:

1. In a sprayer apparatus for carrying on the back of a user and having a back-supporting panel with container means for receiving liquids to be dispensed through liquid flow passage means communicating with a coupling fitting on the bottom of the container means, the apparatus including a stand attached to the panel and having a base portion formed of bent tubing for supporting the apparatus on a surface when worn, the combination comprising:
   support plate means configured for detachably engaging the base portion of the stand;
   means for clamping said support plate means to said base portion;
   battery means and motor-operated pump means attached to said support plate means with the center of gravity thereof generally centrally located relative to said base portion, said pump means having an inlet and an outlet;
   fitting means for attachment to said coupling fitting, said fitting means including liquid flow passages in communication with the liquid flow passage means of said container means; and
   hose means interconnecting the liquid flow passages of said fitting means with said inlet and outlet of said pump means.

2. The apparatus of claim 1 wherein said container means includes a generally centrally disposed pressure vessel within said container means, and wherein said fitting means includes at least one liquid flow passage communicating therewith.

3. The apparatus of claim 2 wherein said coupling fitting comprises an internally threaded pump receiving fitting, of said pressure vessel at a lower end of said pressure vessel, and wherein said fitting means is externally threaded and is threadably and removably secured to said pump receiving fitting, and wherein said support plate means, battery means, motor operated pump means and pump receiving fitting are attachable as a unit, and detachable as a unit, from said container means and stand.

4. The apparatus according to claim 2 wherein said liquid flow passage means of said container means includes a passage communicating with the interior of said container means, and wherein said fitting means includes at least one other liquid flow passage communicating therewith.

5. The apparatus according to claim 4 wherein said at least one liquid flow passage of said fitting means includes valve means for permitting the entry of liquid under pressure from said motor-operated pump means.

6. The apparatus of claim 1 wherein said base portion includes opposing generally parallel side tubing portions and an interconnecting tubing portion opposite said back-supporting panel, and wherein said support plate means is formed of bent metal with side channel portions slidably engaging said side tubing portions.

7. The apparatus of claim 6 wherein said means for clamping includes a plate member attachable to said support plate means, said plate member being configured for clampingly engaging said interconnecting tubing portion.

8. The apparatus of claim 7 wherein said battery means is mounted on said support plate means for positoning in proximity to said back-supporting panel.

9. The apparatus according to claim 8 wherein said coupling fitting is a threaded opening and said fitting means includes a threaded outer surface for engagement therewith.

10. In a sprayer apparatus for carrying on the back of a user, the combination comprising:
    a back-supporting panel configured for abutting relation with the back of the user and adapted to be in a generally vertical position in use;
    container means integrally formed with said panel and configured for receiving liquids to be dispensed;
    a pressure vessel generally centrally disposed within said container means and having a generally vertically extending bottom opening configured to form a coupling fitting;
    first liquid flow passage means communicating with said coupling fitting and the interior of said container means;
    a stand attached to said panel and having a base portion formed of bent tubing for supporting the apparatus on a surface when worn, the base portion including opposing side tubing portions and an interconnecting tubing portion, collectively disposed in a plane generally perpendicular to said panel;
    support plate means configured for detachably engaging the opposing side tubing portions of said base portion;
    means for clamping said support plate means to said interconnecting tubing portion;
    battery means and motor-operated pump means attached to said support plate means with the center of gravity thereof generally centrally located relative to said base portion, the pump of said motor-operated pump means having an inlet and an outlet;
    fitting means for attachment to said coupling fitting, said fitting means including liquid flow passages in communication with the liquid flow passage means of said container means; and
    hose means interconnecting the liquid flow passages of said fitting means with said inlet and outlet of said pump means.

11. The apparatus according to claim 10 wherein said liquid flow passages of said fitting means includes an opening in communication with said pressure vessel and the outlet of said pump means, and valve means mounted on said fitting means for preventing flow of liquid from said pressure vessel to said pump means.

12. The apparatus according to claim 10 wherein said means for clamping includes a plate member attachable to said support plate means, said plate member being configured for clampingly engaging said interconnecting tubing portion.

13. The apparatus of claim 12 wherein said battery means is mounted on said support plate means for positioning in proximity to said back-supporting panel.

14. The apparatus according to claim 13 wherein said coupling fitting is a threaded opening and said fitting means includes a threaded outer surface for engagement therewith.

15. The apparatus according to claim 13 wherein said liquid flow passages of said fitting means includes an opening in communication with said pressure vessel and the outlet of said pump means, and wherein said fitting means includes valve means for enabling flow of liquid under pressure from said pump outlet to the interior of said pressure vessel.

16. A retrofit motorized pump package for a sprayer apparatus adapted to be carried on the back of a user, the sprayer apparatus comprising, a back support panel, container means integrally formed with the panel for receiving liquids to be dispensed, a pressure vessel centrally disposed within the container means and having a bottom opening forming a coupling fitting with liquid flow passage means, a manually operated pump assembly detachably secured to said coupling fitting, and a tubular stand attached to said panel and including a pair of opposing side tubing portions and an interconnecting tubing portion collectively disposed in a plane generally perpendicular to said panel, said retrofit package being adapted to replace said manually operated pump assembly and to be attached to and supported on said stand to thereby provide a motorized liquid sprayer having improved balance and weight distribution and enhanced stability both when carried on the back of a user and when supported by said stand, said retrofit package comprising:

support plate means configured for detachably engaging the opposing side tubing portions of said base portion;

means for clamping said support plate means to said interconnecting tubing portion;

battery means and motor-operated pump means attached to said support plate means with the center of gravity thereof generally centrally located relative to said stand;

fitting means adapted to be connected to and received within said coupling fitting and including liquid flow passages in communication with the liquid flow passages of said coupling fitting of said container means upon connection of said fitting means with said coupling fitting; and means interconnecting the fitting means and the pump means, whereby the sprayer apparatus may be changed from a manual apparatus to a motor driven apparatus by detaching the manual pump assembly from the coupling fitting of the pressure vessel, slidably engaging and connecting the support plate means to the side tubing portions of the stand, and securing the fitting means to the coupling fitting of the pressure vessel.

17. The apparatus of claim 16 wherein said support plate means is formed of a planar member with side channel portions for slidably engaging said side tubing portions.

18. The apparatus of claim 17 wherein said means for clamping includes a plate member attachable to said support plate means, said plate member being configured for clampingly engaging said interconnecting tubing portion.

19. The apparatus of claim 16 wherein said battery means is mounted on said support plate means for positioning in proximity to said back supporting panel.

20. The apparatus according to claim 16 wherein said coupling fitting is a threaded opening and said fitting means includes a threaded outer surface for engagement therewith.

21. The apparatus according to claim 16 wherein said liquid flow passage means of said container means includes a passage communicating with the interior of said container means, and wherein said fitting means includes at least one other liquid flow passage communicating therewith.

22. The apparatus according to claim 21 wherein said at least one liquid flow passage of said fitting means includes valve means for permitting the entry of liquid under pressure from said motor-operated pump means.

* * * * *